United States Patent [19]

Itoga et al.

[11] Patent Number: 5,475,613
[45] Date of Patent: Dec. 12, 1995

[54] ULTRASONIC DEFECT TESTING METHOD AND APPARATUS

[75] Inventors: Kouyu Itoga; Takamasa Ogata; Hideyuki Hirasawa, all of Kobe; Takaya Misumi; Sumihiro Ueda, both of Kakogawa; Osamu Miki, Akashi; Hiroo Owaki; Harutaka Koike, both of Kobe; Yuji Sugita, Chita; Katsuhiro Onda; Takaaki Okumura, both of Nagoya, all of Japan

[73] Assignees: Kawasaki Jukogyo Kabushiki Kaisha, Kobe; Chubu Electric Power Co., Inc., Aichi, both of Japan

[21] Appl. No.: 965,378

[22] PCT Filed: Apr. 18, 1992

[86] PCT No.: PCT/JP92/00501

§ 371 Date: Dec. 17, 1992

§ 102(e) Date: Dec. 17, 1992

[87] PCT Pub. No.: WO92/18862

PCT Pub. Date: Oct. 29, 1992

[30] Foreign Application Priority Data

Apr. 19, 1991 [JP] Japan ................................ 3-113681

[51] Int. Cl.⁶ .................................................. E21B 49/00
[52] U.S. Cl. .............. 364/507; 364/551.01; 364/413.25; 364/474.24; 364/413.22; 364/474.37; 364/474.05; 73/626; 73/611; 73/625; 73/624; 128/661.01; 128/660.07; 128/660.09; 348/135
[58] Field of Search .................. 364/506, 507, 364/413.25, 580, 490, 474.37, 551.01, 550, 474.05, 474.01–474.08, 474.20–474.28; 73/598, 600, 602, 620, 599, 624, 611, 614, 599, 625, 637, 618, 634, 67.7, 67.8, 67.9, 622, 626; 128/660.07, 916, 661.01, 660.08, 660.09

[56] References Cited

U.S. PATENT DOCUMENTS

| | | | |
|---|---|---|---|
| 3,585,851 | 6/1971 | Walther | 73/67.8 |
| 3,646,805 | 3/1972 | Walters | 73/67.5 |
| 3,918,025 | 11/1975 | Koshikawa et al. | 73/67.7 |
| 3,952,150 | 4/1976 | Gerardin et al. | 178/6.8 |
| 4,597,292 | 7/1986 | Fujii et al. | 73/599 |
| 4,615,217 | 10/1986 | Koike et al. | 73/624 |
| 4,747,411 | 5/1988 | Ledley | 364/413.25 |
| 4,752,896 | 6/1988 | Matsumoto | 364/413.25 |
| 4,768,155 | 8/1988 | Takishita et al. | 364/507 |
| 4,835,688 | 5/1989 | Kimura | 364/413.22 |
| 4,843,884 | 7/1989 | House et al. | 73/622 |
| 4,866,614 | 9/1989 | Tam | 364/413.25 |
| 4,880,010 | 11/1989 | Szilard | 128/661.01 |
| 4,977,512 | 12/1990 | Nakagawa | 364/474.37 |
| 5,078,145 | 1/1992 | Furuhata | 128/660.07 |

(List continued on next page.)

FOREIGN PATENT DOCUMENTS

| | | |
|---|---|---|
| 55-53454 | of 0000 | Japan . |
| 53-143293 | 12/1978 | Japan . |
| 57-27691 | 2/1982 | Japan . |
| 61-57854 | 3/1986 | Japan . |
| 61-57853 | 3/1986 | Japan . |
| 62-21014 | 1/1987 | Japan . |
| 394154 | 4/1991 | Japan . |

Primary Examiner—Kevin J. Teska
Assistant Examiner—Jacques H. Louis-Jacques
Attorney, Agent, or Firm—Leydig, Voit & Mayer

[57] ABSTRACT

A three dimensional object under test is measured to obtain shape data representing a shape of the three dimensional object. The object under test is measured using, for example, an ultrasonic probe LED to obtain defect test data. A processing mechanism forms a three-dimensional graphic image of a defect zone from the defect test data and a three-dimensional graphic image of the object under test from the shape data. A display mechanism is provided for displaying the three-dimensional graphic image of the defect zone superimposed over the three-dimensional graphic image of the object under test.

31 Claims, 6 Drawing Sheets

U.S. PATENT DOCUMENTS

| | | | |
|---|---|---|---|
| 5,115,401 | 5/1992 | Oyama et al. | 364/474.37 |
| 5,121,333 | 6/1992 | Riley et al. | 364/474.05 |
| 5,127,037 | 6/1992 | Bynum | 364/413.25 |
| 5,128,870 | 7/1992 | Erdman et al. | 364/474.05 |
| 5,153,721 | 10/1992 | Eino et al. | 358/107 |
| 5,184,306 | 2/1993 | Erdman et al. | 364/474.05 |
| 5,198,990 | 3/1993 | Farzan et al. | 364/474.37 |
| 5,243,265 | 9/1993 | Matsuura et al. | 364/474.37 |
| 5,255,681 | 10/1993 | Ishimura et al. | 128/660.09 |
| 5,257,204 | 10/1993 | Sawada et al. | 364/474.37 |
| 5,327,351 | 7/1994 | Matsuura et al. | 364/474.05 |
| 5,343,402 | 8/1994 | Matsuura et al. | 364/474.37 |

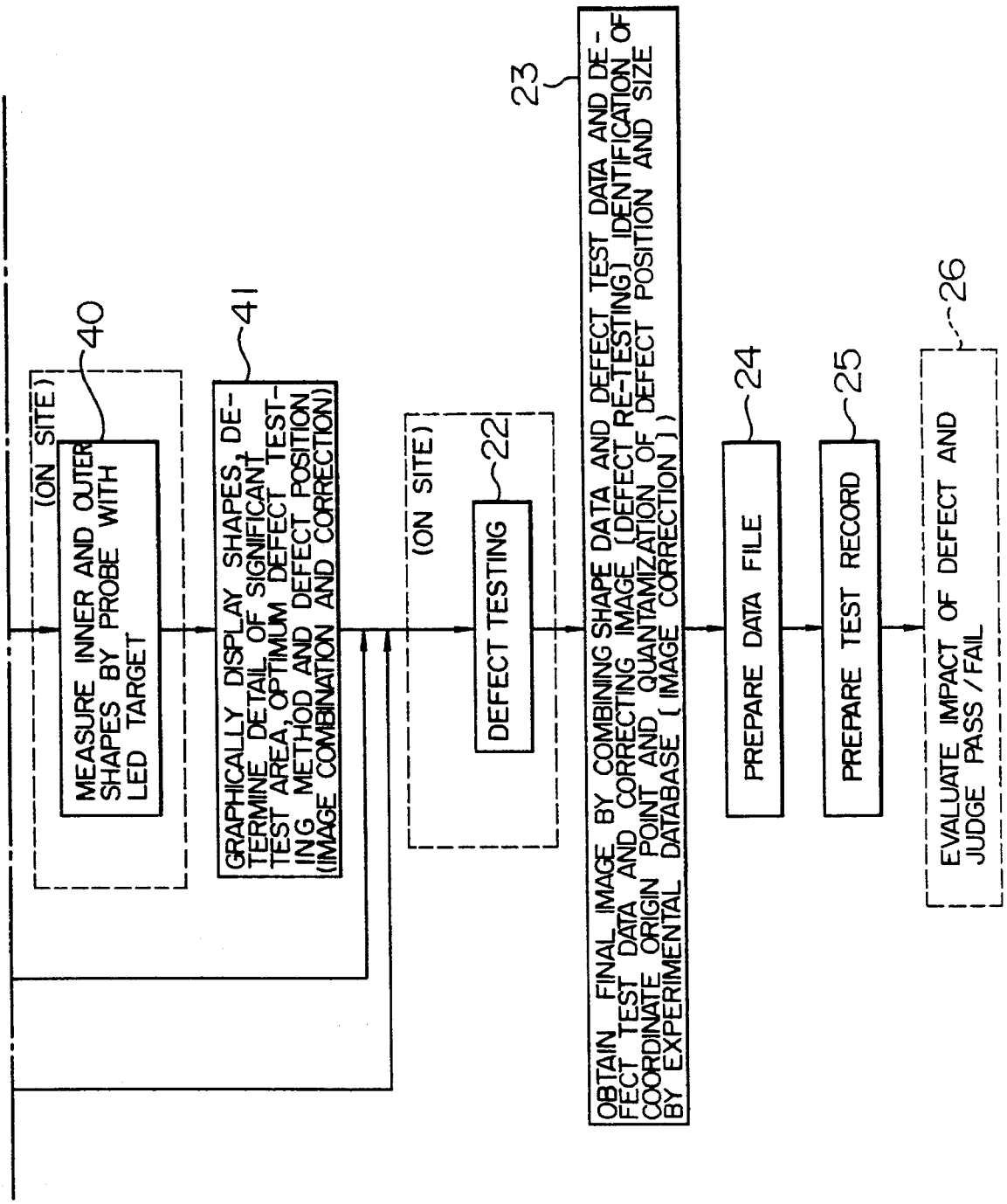

ULTRASONIC DEFECT TESTING METHOD AND APPARATUS

TECHNICAL FIELD

The present invention relates to defect testing method and apparatus using ultrasonic wave, and more particularly to ultrasonic defect testing method and apparatus for a part having a complex three-dimensional free curved shape.

BACKGROUND ART

As is well known, as civilian society has been developed, industries have highly developed and the trend is even rising.

For various equipments which support civilian society and industrial economy, it is required to maintain the inherent functions thereof not only at installation thereof but also over a sufficiently long period.

As chemical technology advances, most of those equipments comprise a plurality of parts to perform complex functions. Accordingly, the assembling and engagement structures are three-dimensional and complex. In order to sufficiently maintain the functions, periodic and non-periodic tests of the functions are essential in addition to the tests at new installation. Depending on actual status of use, a periodic test is legally obliged.

It is desirable to check those equipments at new installation as well as at the periodic or non-periodic function tests during use for the maintenance purpose, by disassembling them into individual parts or part units (hereinafter collectively referred to as parts). However, where the equipment has a complex assembling and engagement structure, the test by disassembling is very troublesome, and does not meet economical requirement, and lowers run efficiency. Under certain circumstances, the test by disassembling may impair the functions of the parts and hence nondestructive testing has been widely used.

Recently, because of the fact that many equipments are made of metals, the nondestructive testing by ultrasonic wave disclosed in JP-A-53-143293, JP-A-577691 and JP-A-62-21014 have been used widely.

Where a part of an equipment is a plane or of simple curved shape such as a pipe, an ultrasonic defect testing system is simple and little skill is required for the test. However, in the recent mechanical equipments for automobiles, ships, aeroplanes and generators, parts are widely used having a complex three-dimensional free curved surface such as a turbine blade, a pump casing, a main steam tube joint, a large size valve or a tube table. Among others, in nuclear facilities, medical facilities and laboratories, it is strongly demanded that those parts of the complex shapes maintain their functions almost perfectly for years. Because of the difficulty of the test by the disassembling, the ultrasonic defect testing of the parts having the complex three-dimensional free curved surfaces is demanded. It is also demanded to record and keep the defect data for subsequent use or for the study of elongation of the lifetime of the same or a similar type of equipment.

However, the ultrasonic defect testing for the part having such a complex three-dimensional free curved surface has an essential shortcoming which cannot be solved by the existing and practiced ultrasonic defect testing system for the part having a simple plane or curved surface.

Since a defect image cannot be superimposed on an image of a part, that is, an image representing a contour of an object under test, it is not possible to discriminate an echo reflected from the contour of the object to be tested from one reflected from the defect. Namely, where there is no image of the object under test, or where there is an image of the object but it includes outer surface corrosion, or where the object under test was not made as the same image as displayed, an optimum defect testing condition cannot be determined unless shapes of inner and outer surfaces are grasped, or it is not possible to decide whether an echo derived by the ultrasonic defect test is one reflected from the inner surface of the object under test or from the defect.

Specifically, the defect testing conditions include a defect testing approach position, a scanning direction, a refraction angle of a probe, an operating frequency of the probe, a dimension of a resonator of the probe, an orientation of the probe and scanning velocity.

An ultrasonic defect testing system for a part having free curved shape which utilizes laser technique and ranging technique by making use of computer technology in order to meet those needs has been developed but it does not still fully meet the inherent needs as is well known technically.

FIGS. 3 and 4 show a test in a system 2 which ultrasonically tests defects a, b and c at deep inner locations such as air bubbles and tear-off in an object 1 under test having a complex three-dimensional free curved surface such as a turbine blade. As shown in FIG. 3, a laser range finder 3 is mounted on a hand 4 of a robot as a probe to measure surface shape of the object 1 under test in the air. The robot hand 4 is driven by a six-axis synchronized drive unit 5 which is controlled by a personal computer 6 to measure the shape of the object 1 under test. The measurement data is processed by a mini-computer 7.

Then, the defects a, b and c of the object 1 under test are ultrasonically tested in the water by an ultrasonic defect testing apparatus 8. An operation of a probe is controlled by the mini-computer 7 which calculates paths on the basis of shape measurement data of the object 1 under test by use of the laser range finder 4. As shown in FIG. 4, an upper half of the object 1 under test is displayed as a rectangular image 10' on a screen 10 of the mini-computer 7. Defect images a', b' and c' corresponding to the defects a, b and c are shown in the image 10' of FIG. 4. Numeral 9 in FIG. 3 denotes an image analyzing unit for analyzing images the basis of the data from the ultrasonic defect testing apparatus and the data from the synchronous drive unit 5.

In the ultrasonic defect testing method for the deep defect zone of the object under test which has three-dimensional free curved surface shape in the prior art system, the three-dimensional defect testing to the deep defect zones of the object under test is basically the scanning by a probe which is done on the basis of the measurement of the outer free curved surface of the object under test. Accordingly, in actual, the image display 10' of the object under test shown in FIG. 4 is a plane display (depth is not displayed) and is not a three-dimensional display. Accordingly, the measurement of the relative position, the inclination and the size of the defect in the deep areas of the three-dimensional shape of the object under test, and data analysis by the probe are not attained. Further, because of mono-chromatic display, the discrimination performance is poor.

Because the display of the defect test image 10' is a rectangular developed image as shown in FIG. 4, the overall shape including the inner and outer three-dimensional shapes of the object under test is not displayed. Further, though the outer surface is displayed, the shape of the inner surface or the rear surface which include the defect are not measured.

Because of the two systems that the measurement is done in the air and that the defect testing is done in the water, working environments for the shape measurement and the defect testing are different. The mounting and the removal of the object 1 under test are very troublesome, and the adjustment is inconvenient and inefficient.

When the dipping status of the object 1 under test is not good and the application of water jet in front of and behind the object under test is not good, alternative process is very difficult to attain.

In the prior art method, since the defects of the object under test is ultrasonically tested while the object is immersed in the water, the object to be tested is limited to a ceramic product or a small object, and freedom of handling is low.

Further, since shapes of the inner and outer surfaces of the object under test are not measured, the image display on the screen is not three-dimensional and a propagation path of the ultrasonic wave cannot be analyzed. Accordingly, the defect testing condition for the three-dimensional shape of the object under test cannot be instantly determined.

In addition, because the measurement data cannot be displayed on the screen on real time basis, discrimination of the defects is not easy and not efficient.

Further, as described above in connection with the defect testing, it is difficult to discriminate the echo from the inner shape or the rear shape of the object under test from the echo from the inherent defect.

Further, since the beam is irradiated by the spotwise coordinate extraction when the shape measurement by the laser or the defect testing by the ultrasonic probe is to be conducted, the entire area cannot be simultaneously covered because of the size of the beam. Where the object under test includes fine unevenness, the shape measured by the laser does not match to the shape required for the ultrasonic defect testing, and the position and the direction of the probe are not determined. In addition to the spotwise coordinate extraction, the derived echo must be corrected. As a result, accurate processing is not attained.

Further, since the six-axis synchronous drive unit is used, the freedom of scanning of the probe and the freedom of the scanning area are small.

Further, since the object under test is displayed by the rectangular image display, the above leads to the disability of the three-dimensional discrimination and detection of the defect testing ultrasonic echo.

DISCLOSURE OF THE INVENTION

It is an object of the present invention to provide ultrasonic defect testing method and apparatus which permit exact testing of defects even when an object under test having a complex three-dimensional free curved surface is tested by an ultrasonic wave.

It is another object of the present invention to provide ultrasonic defect testing method and apparatus which permit three-dimensional display of the defect.

It is another object of the present invention to provide ultrasonic defect testing method and apparatus which permit real time display of the defect.

It is another object of the present invention to provide ultrasonic defect testing method and apparatus which facilitate handling an object under test.

In accordance with the present invention, problems in the system of the nondestructive ultrasonic defect testing to internal defects such as air bubbles, cracks or tear-off at a complex area which imparts a great impact when it falls during new installation or subsequent run of parts of an equipment having the three-dimensional free curved surface which is widely used in various manufacturing facilities, are solved. Namely, while the advantages of the ultrasonic defect testing are fully utilized, the mutual positional relation of the defect to the three-dimensional shape having the complex free curved surface of the part under test for the defect can be three-dimensionally detected. The ultrasonic defect testing condition can be fully discussed and exact three-dimensional defect testing is attained. Test environment for the entire defect testing need not be changed and the processing means is very smoothly operated. The result of the defect testing can be measured on real time basis and recognized visually, and the operation is very easy. The defect test data can be used as reference data for the defect testing of subsequent equipments or other similar products.

The present invention can be suitably applied to the three-dimensional testing by the ultrasonic wave of defects in a thick part which may affect to aging functions such as air bubbles, cracks or tear-off in the part (including unit parts) having a complex three-dimensional free curved surface built in an equipment which is used in nuclear facilities or various machine manufacturing plants. In this case, a probe is mounted at an end of a manually operated or robotic multi-articulation hand, and a plurality of LED's are mounted on the probe and they are measured by a charge coupled device CCD camera or a position sensitive device (PSD camera). An outer contour, internal and rear surface three-dimensional shapes of a thick part of an object under test are measured. The measurement data is displayed as three-dimensional graphic images (more strictly, a projection of a three-dimensional shape onto a two-dimensional screen) by a computer to determine defect testing conditions. The ultrasonic testing is conducted in accordance with the testing conditions and the resulting data is displayed as three-dimensional graphic images and recorded on real time basis. In this manner, the object under test, that is, the complex curved surface of the object under test is three-dimensionally grasped and the defect is recognized. Further, it may be recorded for subsequent use as reference data.

BRIEF DESCRIPTION OF THE DRAWINGS

FIGS. 5a and 5b show flow charts of a defect testing method in the system shown in FIG. 1.

BEST MODE FOR CARRYING OUT THE INVENTION

One embodiment of the present invention is now explained with reference to FIGS. 1 and 2.

Figure 3:
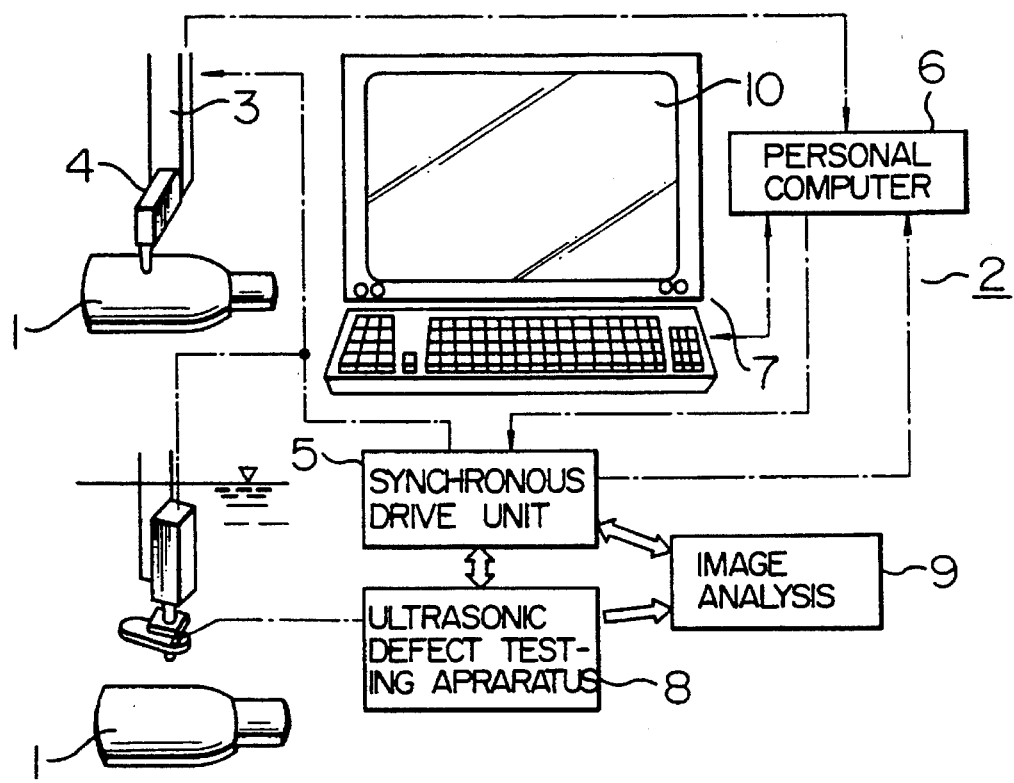
FIG. 3 shows a schematic view of a prior art ultrasonic defect testing system for the object under test displayed on the screen.
Figure 4:
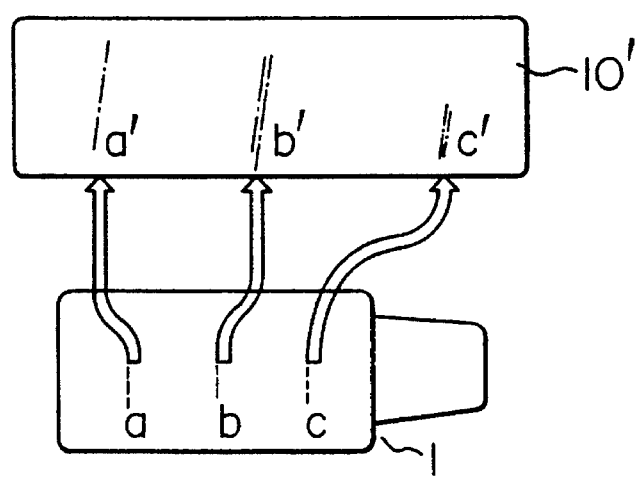
FIG. 4 shows a schematic view of defect display by the system shown in FIG. 3.

The like elements to those shown in FIGS. 3 and 4 are designated by the like numerals.

Figure 1:
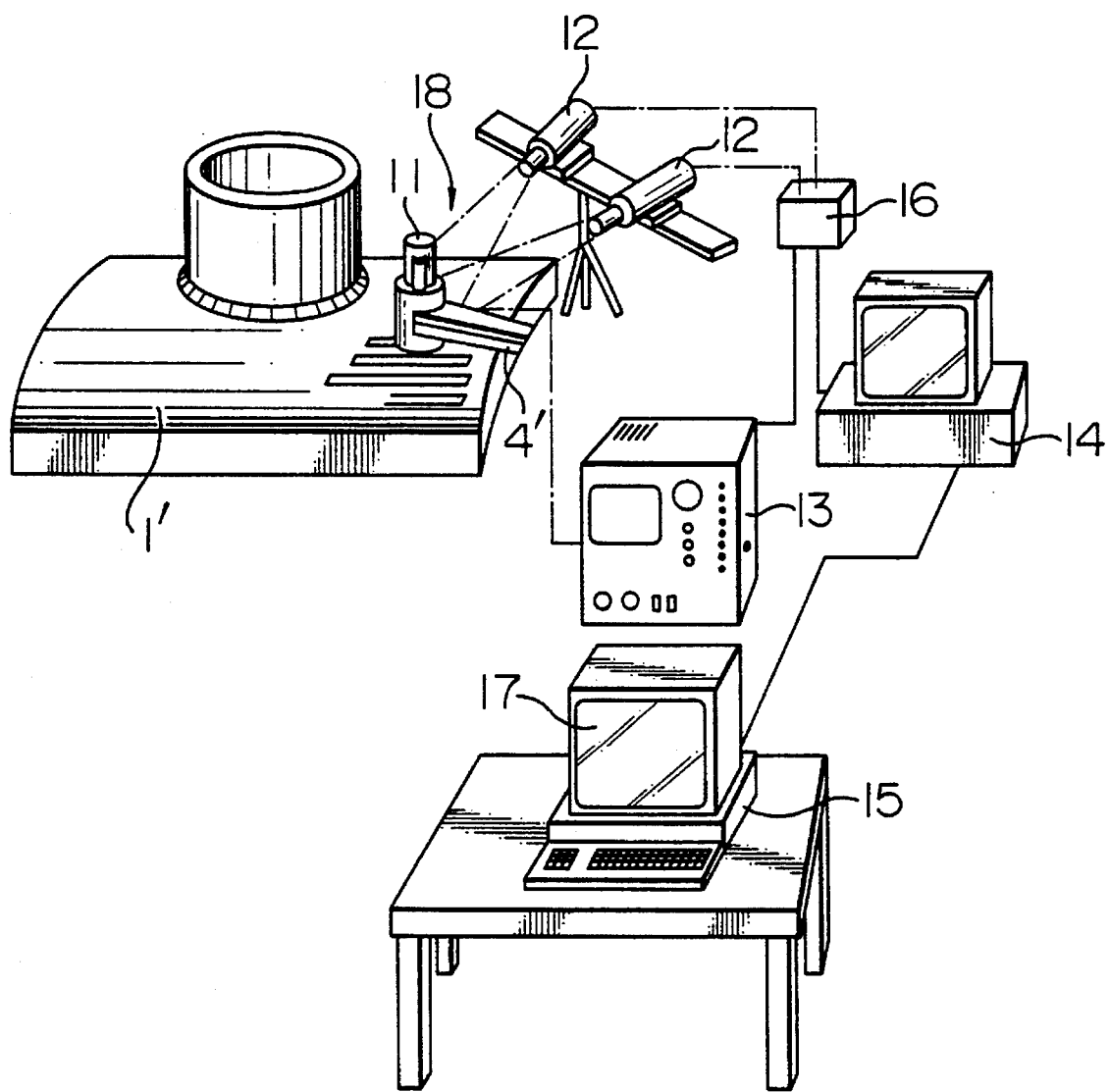
FIG. 1 shows a schematic perspective view of an embodiment and an ultrasonic defect testing system of the present invention.

FIG. 1 shows an ultrasonic defect testing system used in the present invention. It is used to ultrasonically test a defect such as air bubbles, cracks or tear-off in a thick area of an object 1' under test of a complex three-dimensional shape having a complex three-dimensional shown in FIG. 2.

In FIG. 1, the dimensions of the object 1' under test and various measurement equipments are schematically deformed for the purpose of illustration.

Positional attitude of the outer contour of the complex three-dimensional curved surface of the object 1' under test is measured by one or more CCD or PSD (position sensitive device) cameras 12 having a plurality of (three in the present embodiment) of light emitting diodes (LED's) 11 arranged on an ultrasonic probe 4' or by a laser beam in the same manner as that of prior art. The measured data is read into a measurement recorder 16 for recording. The CCD or PSD camera 12 is arranged to face the LED 11 to detect the position and posture of the LED's 11, and the thickness and the inner surface of the object 1' under test are measured and the data is read into and recorded in the measurement recorder 16 (sensor processor). Three or more LED's 11 are mounted on the probe 4' to form a scanner 18. The positional data of the three or more LED's 11 is read to determine the position and posture of the end of the probe 4' of the scanner 18, and calculate an incident point of the ultrasonic wave from the probe 4'.

The detection of the LED's 11 and the CCD or PSD camera 12 may be substituted by the shape measurement by manipulating mechanical jigs having an encoder mounted thereon. However, from the standpoint of freedom of scanning and scanning range, the measurement by the LED's is much preferable in terms of precision.

One of features of the present invention resides in the scanner in which three or more LED's for measuring the outer contour of the object under test are integrally mounted on the ultrasonic probe. By scanning the object under test by the scanner, the relationship between the measurement of the ultrasonic probe and the position and posture of the probe on the object under test can be exactly determined.

Through the use of the range finding function of the ultrasonic probe, the inner contour of the object under test can be determined by the probe while the outer contour of the object under test is measured by the three or more LED's.

Through the use of the defect testing function of the ultrasonic probe, the defect of the object under test can be tested by the probe while the outer contour of the object under test is measured by the three or more LED's.

Figure 2:
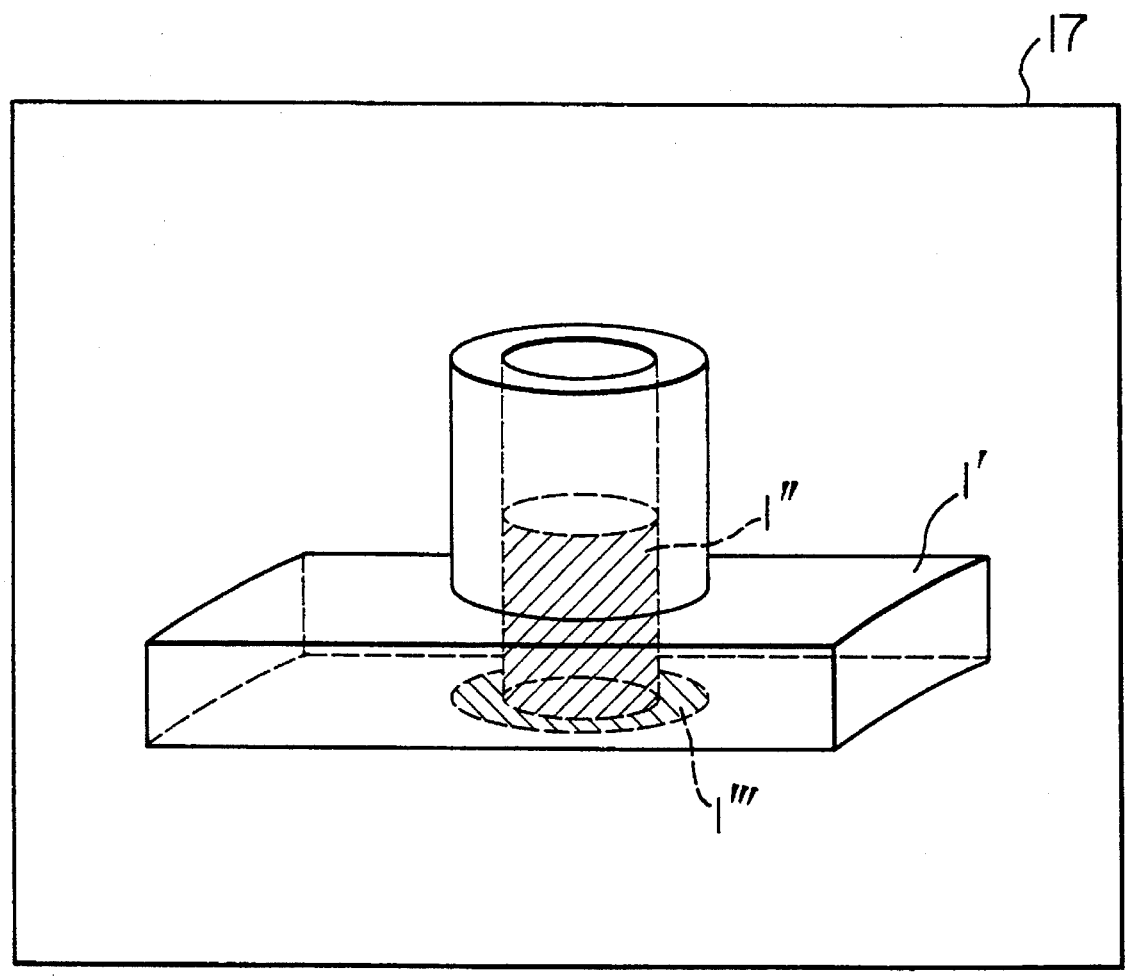
FIG. 2 shows an image display of an object under test.

Defect means 1'' and 1''' of the object 1' under test as shown in FIG. 2 are determined as significant defect zones by use of past defect testing data previously stored or data on the basis of the experience of operators or prediction such as analysis of stress concentration, and they are inputted to a computer 15.

On the basis of the three-dimensional free curved surface contour such as the outer contour, thickness and rear surface (inner surface) shape of the object 1' under test inputted to the measurement recorder 14 by the computer 15, the geometrical defect location conditions (methods) for the defects 1'' and 1''' such as a propagation path of the ultrasonic wave and the defect test area in the next stage ultrasonic defect testing are determined, the probe 4' is pressed to the outer surface of the object 1' under test with predetermined pressure to scan the object by the probe 4'.

The scanning may be done manually or by a robot. In the robotic operation, the probe 4' is scanned with the predetermined pressure so that variation of data due to variation of the pressure is avoided. Through the use of a direct contact method of the probe 4' to the outer surface of the object 1' under test, the defect of the large and free size object 1' can be tested, and the on-site defect testing can be attained even in a narrow site by use of the installed system.

On the basis of the outer and inner surface contour measurement data including the thickness of the object 1' under test, the ultrasonic defect testing conditions (methods) are determined by the computer 15. Manual defect testing or robot-controlled one is conducted in accordance with the conditions.

In this case, optimum defect testing conditions and determination methods by a data-base such as acoustic theory, elastic wave analysis and model experiment may be previously inputted to the computer 15.

Figure 6:
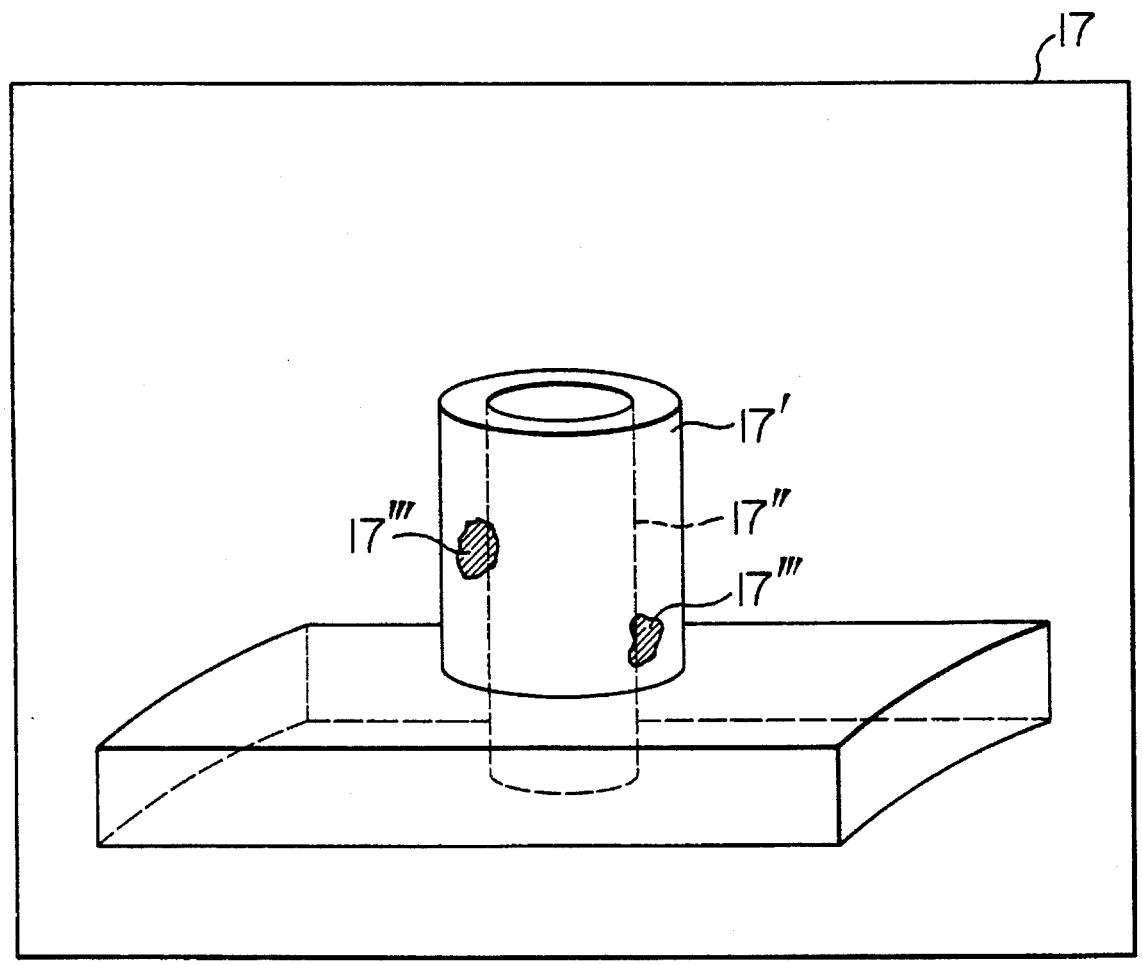
FIG. 6 shows an image display of an object under test which includes a defect.

Three-dimensional shapes 17' and 17'' of the object 1' under test are displayed on a screen 17 shown in FIG. 6 by a three-dimensional graphic image display 17, and a defect 17''' detected by ultrasonic testing with the probe 4' is superimposed thereon and, if desired, they are displayed by a multi-colored image. The super-imposition is attained by matching the origin coordinates and the directions of the axes of the shape of the object under test to those in defect testing.

In this case, by coloring the image displays of the contour of the object 1' under test and the defect by different colors (for example, yellow for the outer contour and red for the defect) by the three-dimensional graphic device 15, the relative position and the sizes of the defect can be clearly distinguished from the outer contour of the object 1' under test.

In this case, the object 1' under test and the defect may be separately displayed and recorded, or displayed and recorded in superposition for use as reference data of the next ultrasonic defect testing of the object 1' under test or the ultrasonic defect testing to a similar object under test.

By measuring the shape of the object 1' under test in the air, the ultrasonic testing can be carried out, avoiding environmental variation of the defect measurement and parts which are not suitable for the measurement in the water can be measured in the air.

Since the ultrasonic defect testing conditions are predetermined as described above and the multi-color three-dimensional graphic image is displayed on real time basis, the interior of the object 1' under test can be thoroughly tested. Accordingly, an echo due to the defect can be clearly discriminated from an echo due to the shape of the object under test and the object can be thoroughly tested.

The manner of embodiment of the present invention should not be limited to the above embodiment. For example, the object work is not limited to the tube mount but it may be a pump casing, a main steam tube joint, a large size valve, etc.

As an alternative design, the probe to the object under test may be of non-contact type instead of contact type. It is within a range of design alternative.

An operation of an embodiment of the ultrasonic defect testing method of the present invention is now explained with reference to flow charts shown in FIGS. 5a and 5b.

Figure 5A:
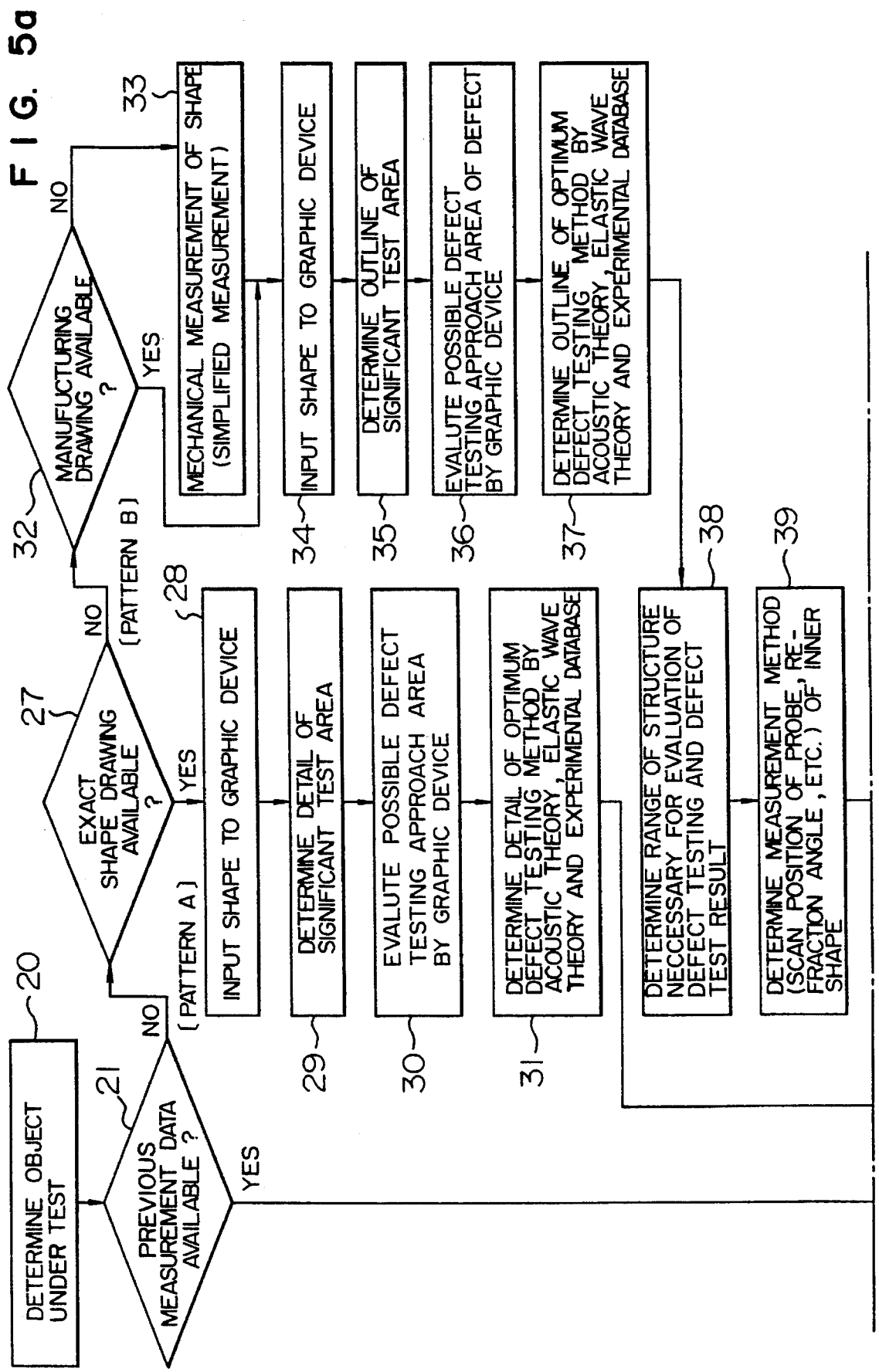

In FIGS. 5a and 5b, the object 1' under test is identified in a step 20. In a step 21, the data base stored in the measurement recorder 14 or the computer 15 is searched to decide whether the three-dimensional shape of the identified object 1' under test has previously been measured or not. If there is the measurement data of the shape of the object 1' under test, the process proceeds to a step 22 to test the object by the ultrasonic wave. When the defect testing is completed, the shape data of the object 1' under test and the defect data are combined in a step 23 and the status 17''' of the defect is displayed on the display screen 17 in superposition to the displays 17' and 17'' of the object 1' under test having the three-dimensional shape. In a step 24, each and/or combined data of the shape data and the defect data are filed in a predetermined file format. In a step 25, they are stored in an external storage, not shown, as test record. The test record may be used, as required, for the evaluation of the affect of the defect and the judgement to meet the requirement.

In the step 21, if there is not the measurement data of the shape of the object 1' under test, the process proceeds to a step 27. In the step 27, it is decided whether the shape of the object 1' under test has been reserved as data which permits to derive exact thickness by using a CAD system or not. If the data which represents the exact shape is present, the process proceeds to a step 28. In the step 28, the data which represents the exact shape is inputted to the computer 15. In a step 29, significant test zones 1'' and 1''' which are to be tested in the object 1' under test are determined on the basis of the input shape data. In a step 30, the evaluation of the defect testing approach area in the defect testing is checked by the computer 15. In a step 31, the optimum defect location condition (method) using the ultrasonic probe is determined. When the defect testing condition is determined, the process proceeds to a step 22 to execute the steps described above.

On the other hand, in the step 27, if there is not the exact data on the shape of the object 1' under test, the process proceeds to a step 32. In the step 32, it is decided whether the shape data like a contour chart of the object 1' under test is available or not. If such shape data is not available, the process proceeds to a step 33 to conduct mechanical simplified measurement. Then, steps 34 to 37 are executed.

In the step 32, if the shape data like the contour chart of the object 1' under test is available, the steps 34–37 are executed in accordance with the shape data. The steps 34–37 are essentially identical to the steps 28–31, respectively.

In the step 37, when the defect testing condition (method) is determined, the process proceeds to a step 38. In the step 38, a condition (range) of a device (structure) necessary for the defect testing is determined. In a step 39, a method for measuring the inner contour of the object 1' to be tested is determined. In a step 40, exact shape data which represents the outer and inner shapes of the object 1' under test are obtained by use of the probe with the LED's target. In a step 41, the object 1' under test is graphically displayed by use of the shape data and the locations of the defects are specifically determined. Then, the process proceeds to the step 22 to execute the steps 22 to 26 described above.

In accordance with the present invention, in the nondestructive ultrasonic defect testing to the structure having the three-dimensional complex curved surface of the unit equipment to be used in various equipments of the aircraft, the ship, the automobile or the nuclear facilities, the shape and the internal measurement are combined in accordance with the measurement data and it is displayed by the multi-color three-dimensional graphics so that the outer contour of the object under test as well as the relative position and attitude of the defect to the inner and outer contour and the size thereof are displayed by images. By displaying them by different colors, the overall can be grasped and the relative discrimination of the defect to the overall can be clearly measured on real time basis.

Accordingly, in the ultrasonic defect testing, the three-dimensional location of the defect in the object under test can be grasped and the defect can be securely detected.

Since it is possible to measure the propagation path of the ultrasonic wave during the defect testing, the optimum ultrasonic defect testing condition and method for the object under test can be determined to assure that the optimum defect location is exactly conducted as designed.

Since the data is instantly recorded, it can be used as powerful backup data for the subsequent defect testing or the ultrasonic defect testing for a similar part.

The contour measurement by the contour measurement apparatus which includes the combination of the laser or the ultrasonic probe having the LED's mounted thereon and the CCD (PSD) can measure the outer contour of the object under test by the ultrasonic thickness measurement as well as the thickness and the inner contour. Thus, the defect can be relatively displayed in the three-dimensional graphic image display so that the scan operation by the operator can be carried out directly and exactly.

Since the measurement and the ultrasonic defect testing can be done in one environment rather than different environments such as in the air and in the water, the environmental application condition of the object under test is not selected and the freedom of defect testing is significantly increased.

Accordingly, the flexibility to permit the easy defect testing without regard to the size and the shape of the object under test is enhanced.

The ultrasonic defect testing data is corrected for the shape measurement data of the object under test to display it with the three-dimensional graphic image and record it. Thus, the position and attitude of the probe can be measured, the direction of incidence of the ultrasonic wave is made clear and the correction of the direction of incidence by the conventional two-dimensional display is not necessary.

INDUSTRIAL APPLICABILITY

In accordance with the present invention, the exact defect testing to the part of the equipments in the nuclear facilities, the medical facilities and the laboratories as well as the part having the complex three-dimensional curved surface in any industrial fields can be effected.

We claim:

1. An ultrasonic defect testing method for testing an object having a three-dimensional curved surface comprising the steps of:

(a) measuring a three-dimensional shape of the object under test to acquire shape data representing the shape thereof;

(b) measuring a defect of the object under test by three-dimensionally scanning the object with an ultrasonic probe to obtain defect test data representing a defect testing result;

(c) monitoring the ultrasonic probe to contactlessly measure a three-dimensional position of the ultrasonic probe to obtain positional information of the ultrasonic probe; and (d) displaying on a display screen a combined image in which, by utilizing the positional information of the ultrasonic probe, a three-dimensional graphic image of a defect zone prepared using the defect test data is superimposed on a three-dimensional graphic image of the object under test prepared using the shape data.

2. An ultrasonic defect testing method according to claim 1, wherein, in said step (a), the shape data is acquired by measuring an outer shape of the object under test.

3. An ultrasonic defect testing method according to claim 1, wherein, in said step (a), the shape data is acquired by measuring an inner shape of the object under test.

4. An ultrasonic defect testing method according to claim 1, wherein, in said step (a), the shape data is acquired by measuring inner and outer shapes of the object under test.

5. An ultrasonic defect testing method according to claim 1 wherein a method of measurement suitable for obtaining the defect test data in said step (b) is determined in accordance with the measurement in said step (a).

6. An ultrasonic defect testing method according to claim 5, wherein at least one of an approach position, a scan direction, a scan velocity, a refraction angle, a direction, an operating frequency and a dimension of a resonator of the ultrasonic probe is selected as the defect location method.

7. An ultrasonic defect testing method according to claim 1 wherein, in said step (d), multicolor is used to display the combined image.

8. An ultrasonic defect testing method according to claim 1, wherein, in said step (a), the shape data is obtained by measuring an outer shape of the object under test by touch sensor means.

9. An ultrasonic testing method according to claim 1, wherein said step (a) includes the sub-steps of:

(a1) scanning an outer surface of the three-dimensional shape of the object under test with a scanner having the ultrasonic probe having at least three light emitting diodes (LED's) mounted thereon; and (a2) detecting lights projected by the LED's of the scanner with a position sensitive device (PSD) or charge coupled device (CCD) camera and calculating a position and a posture of an end of the probe to obtain the shape data of the outer surface of the object under test.

10. An ultrasonic defect testing method according to claim 9, wherein the shape data of the outer surface of the object under test by use of the LED's and the defect test data of the object under test with the ultrasonic probe are simultaneously obtained through the scan of the scanner.

11. An ultrasonic defect testing method according to claim 1, wherein said step (a) includes the substeps of:

(a1) scanning an outer surface of the three-dimensional shape of the object under test with a scanner having the ultrasonic probe having at least three light emitting diodes (LED's) mounted thereon;

(a2) detecting lights projected by the LED's of the scanner with a position sensitive device (PSD) or charge coupled device (CCD) camera and calculating a position and a posture of an end of the probe to obtain the shape data of the outer surface of the object under test; and (a3) obtaining the shape data of an inner surface of the object under test by use of the ultrasonic probe for the distance measurement.

12. An ultrasonic defect testing method according to claim 11, wherein the shape data of the outer surface of the object under test by using the LED's and the defect test data of the object under test with the ultrasonic probe are simultaneously obtained through the scan of the scanner.

13. An ultrasonic defect testing method according to claim 1, wherein said step (a) includes the substeps of:

(a1) scanning an outer surface and an inner surface of the three-dimensional shape of the object under test with a scanner having the ultrasonic probe having at least three light emitting diodes (LED's) mounted thereon; and (a2) detecting lights projected by the LED's of the scanner with a position sensitive device (PSD) of a charge coupled device (CCD) camera and calculating a position and a posture of an end of the probe to obtain the shape of the outer surface and the inner surface of the object under test.

14. An ultrasonic defect testing method for an object having a three-dimensional curved surface, comprising the steps of:

(a) scanning the object under test with a scanner having an ultrasonic probe having at least three LED's mounted thereon;

(b) detecting the at least three light emitting diodes (LED's of the scanner with a position sensitive device (PSD) or charge coupled device (CCD) camera and measuring a three-dimensional shape of the object under test to obtain shape data representing a shape thereof;

(c) testing a defect of the object under test by use of the ultrasonic probe of the scanner to obtain defect test data representing a defect testing result; and (d) three-dimensionally determining a position of a defect zone in the object under test on the basis of the shape data and the defect test data.

15. An ultrasonic defect testing method according to claim 14, wherein a three-dimensional positional relationship between the object under test and the defect zone obtained in said step (d) is three-dimensionally graphically displayed on a display screen.

16. An ultrasonic defect testing method for testing an object having a three-dimensional curved surface comprising the steps of:

(a) reading shape data representing a three-dimensional shape of the object under test from a storage;

(b) examining the object under test for a defect by three-dimensionally scanning the object with an ultrasonic probe to obtain defect data representing a defect test result;

(c) monitoring the ultrasonic probe to contactlessly measure a three-dimensional position of the ultrasonic probe, to obtain positional information of the ultrasonic probe; and (d) three-dimensionally determining a position of a defect zone in the object under test on the basis of the shape data and the defect test data, by utilizing the positional information of the ultrasonic probe.

17. An ultrasonic defect testing method according to claim 16, wherein said step (b) includes the sub-steps of:

(b1) scanning an outer surface of the three-dimensional shape of the object under test with a scanner including the ultrasonic probe and at least three light emitting diodes (LED's) mounted on the scanner;

(b2) detecting projected lights from the LED's of the scanner with a position sensitive device (PSD) or charge coupled device (CCD) camera and calculating a position and a posture of an end of the ultrasonic probe to obtain positions of the ultrasonic probe with respect to the shape data of the outer surface of the object under test; and (b3) correlating the defect test data to the position of the scanner on the object under test.

18. An ultrasonic defect testing apparatus for an object having a three-dimensional curved surface, comprising:

means for measuring a three-dimensional shape of the object under test to obtain shape data representing a shape thereof;

an ultrasonic probe for measuring the object under test to obtain defect test data representing a defect testing result by three-dimensionally scanning the object with the ultrasonic probe;

means for monitoring the ultrasonic probe to contactlessly measure a three-dimensional position of the ultrasonic probe, to thereby obtain positional information of the ultrasonic probe;

means for preparing combined image information by utilizing the positional information of the ultrasonic probe to superimpose a three-dimensional graphic image of a defect zone prepared on the basis of the defect test data on a three-dimensional graphic image of the object under test prepared on the basis of the shape data; and means for displaying a combined image on a display screen in accordance with the combined image information.

19. An ultrasonic defect testing apparatus according to claim 18, wherein said means for obtaining the shape data includes shape data of at least one of an outer surface and an inner surface of the object under test.

20. An ultrasonic defect testing apparatus according to claim 18, further comprising means for determining a defect testing method for the ultrasonic probe in accordance with the shape data.

21. An ultrasonic defect testing apparatus according to claim 20, wherein at least one of an approach position, a scan direction, a scan velocity, a refraction angle, a direction, an operating frequency and a dimension of a resonator of the ultrasonic probe is selected as the defect testing method.

22. An ultrasonic defect testing apparatus according to claim 18, wherein said means for preparing the combined image information permits multi-color display of the combined image.

23. An ultrasonic defect testing apparatus according to claim 18, wherein said means for obtaining the shape data includes a scanner having at least three light emitting diodes (LED's) mounted on the ultrasonic probe, means for scanning a three-dimensional outer surface of the object under test with the scanner, means for detecting lights projected by the LED's of the scanner, and means for calculating a position and a posture of an end of the probe to obtain the shape data of the outer surface of the object under test.

24. An ultrasonic defect testing apparatus according to claim 23, wherein the shape data of the outer surface of the object under test obtained using the LED's and the defect test data of the object under test obtained using the ultrasonic probe are simultaneously obtained through the scan of the scanner.

25. An ultrasonic defect testing apparatus according to claim 18, wherein said means for obtaining the shape data includes a scanner having at least three LED's mounted on the ultrasonic probe, means for scanning a three-dimensional outer surface of the object under test with the scanner, means for detecting lights projected by the LED's of the scanner means for calculating a position and a posture of an end of the probe to obtain the shape data of the outer surface of the object under test, and means for obtaining shape data of an inner surface of the object under test by use of the ultrasonic probe for distance measurement.

26. An ultrasonic defect testing apparatus according to claim 25, wherein the shape data of the outer surface of the object under test obtained using the LED's and the shape data of the inner surface of the object under test obtained using the ultrasonic probe are simultaneously obtained through the scan of the scanner.

27. An ultrasonic defect testing apparatus according to claim 18, wherein said means for obtaining the shape data includes a scanner having at least three light emitting diodes (LED's) mounted on the ultrasonic probe, means for scanning three-dimensional outer surface and inner surface of the object under test with the scanner, means for detecting lights projected by the LED's of the scanner, and means for calculating a position and a posture of an end of the probe to obtain the shape data of the outer surface and the inner surface of the object under test.

28. An ultrasonic defect testing apparatus for an object having a three-dimensional curved surface, comprising:

a scanner having at least three light emitting diodes (LED's) mounted on an ultrasonic probe;

means for scanning the object under test by said scanner;

means for detecting projected lights from the at least three LED's of said scanner;

means for measuring a three-dimensional shape of the object under test on the basis of the output from said detection means to obtain shape data representing the shape thereof;

means for testing a defect of the object under test by use of the ultrasonic probe of said scanner to obtain defect test data representing a defect test result; and means for three-dimensionally determining a position of a defect zone in the object under test on the basis of the shape data and the defect test data.

29. An ultrasonic defect testing apparatus according to claim 28, further comprising display means for three-dimensionally graphically displaying on a display screen a three-dimensional positional relationship between the object under test and the defect zone in response to the output from said means for determining the position.

30. An ultrasonic defect testing apparatus for an object having a three-dimensional curved surface, comprising:

means for reading shape data representing a three-dimensional shape of the object under test from a storage;

an ultrasonic probe;

means for testing a defect of the object under test by three-dimensionally scanning the object with the ultrasonic probe to obtain defect test data representing a defect test result;

means for monitoring the ultrasonic probe to contactlessly measure a three-dimensional position of the ultrasonic probe, to thereby obtain positional information of the ultrasonic probe; and means for three-dimensionally determining a position of the defect zone in the object under test on the basis of the shape data and the defect test data, by utilizing the positional information of the ultrasonic probe.

31. An ultrasonic defect testing apparatus according to claim 30 further comprising:

a scanner having at least three light emitting diodes (LED's) mounted on the ultrasonic probe;

means for scanning an outer surface of the three-dimensional shape of the object under test with said scanner;

means for detecting lights projected by the LED's of the scanner;

means for calculating a position and a posture of an end of the probe to determine the position of the scanner at the input shape data; and means for correlating the defect test data to the position of the scanner on the object under test.

* * * * *

UNITED STATES PATENT AND TRADEMARK OFFICE
CERTIFICATE OF CORRECTION

PATENT NO. : 5,475,613
DATED : December 12, 1995
INVENTOR(S) : Itoga et al.

It is certified that error appears in the above-indentified patent and that said Letters Patent is hereby corrected as shown below:

Column 10,

Line 14, change "(LED's" to

--(LED's)--.

Signed and Sealed this

Twenty-third Day of July, 1996

Attest:

BRUCE LEHMAN

Attesting Officer       Commissioner of Patents and Trademarks